United States Patent [19]

Herz et al.

[11] Patent Number: 4,782,013

[45] Date of Patent: Nov. 1, 1988

[54] PHOTOGRAPHIC ELEMENT CONTAINING A MACROCYCLIC ETHER COMPOUND

[75] Inventors: Arthur H. Herz; Roger L. Klaus, both of Rochester, N.Y.

[73] Assignee: Eastman Kodak Company, Rochester, N.Y.

[21] Appl. No.: 77,131

[22] Filed: Jul. 23, 1987

[51] Int. Cl.$^4$ .................... C07D 285/00; G03C 5/24; G03C 1/02; G03C 1/06

[52] U.S. Cl. .................................. 430/564; 430/234; 430/251; 430/428; 430/486; 430/487; 430/566; 549/11; 549/347

[58] Field of Search ............... 430/564, 487, 486, 251, 430/234, 428, 566; 260/330

[56] References Cited

U.S. PATENT DOCUMENTS

| | | | |
|---|---|---|---|
| 3,062,646 | 11/1962 | Dann et al. | 96/66 |
| 3,271,157 | 9/1966 | McBride | 96/107 |
| 4,107,170 | 8/1978 | Garber | 548/199 |
| 4,267,256 | 5/1981 | Bloom et al. | 430/234 |
| 4,311,638 | 1/1982 | Bloom et al. | 540/467 |
| 4,335,185 | 10/1982 | Bergthaller et al. | 568/45 |

FOREIGN PATENT DOCUMENTS 0216973 4/1987 European Pat. Off. .

OTHER PUBLICATIONS

Photographic Science and Engineering vol. 27, No. 1, 1983, R. Mingel (application p. 1, ll. 10-11).

*Primary Examiner*—Mukund J. Shah
*Attorney, Agent, or Firm*—Thomas F. Kirkchoff

[57] ABSTRACT

This invention is directed to a photographic element containing a radiation-sensitive silver halide emulsion layer and a macrocyclic thia or selena ether compound which also comprises oxygen atoms. These macrocyclic compounds are improved silver halide ripening agents.

10 Claims, No Drawings

PHOTOGRAPHIC ELEMENT CONTAINING A MACROCYCLIC ETHER COMPOUND

This invention relates to a photographic element containing a radiation sensitive silver halide emulsion layer comprising a macrocyclic ether compound. More particularly, this invention relates to a photographic element comprising a silver halide emulsion and a macrocyclic thia or selena ether compound.

It is known from *Photographic Science and Engineering*, Vol. 27, No. 1, 1983, R. Hengel, that macrocyclic polyether compounds do not accelerate ripening of photographic emulsions unless one or more of their cyclic oxygen atoms are replaced with nitrogen or sulfur atoms. It is also known that addition of a macrocyclic polyether compound to various stages of preparation of a silver halide emulsion can impart improvements to silver halide properties. For example, U.S. Pat. No. 3,062,646 describes macrocyclic thioether compounds which are useful as sensitizing agents for silver halide. U.S. Pat. No. 3,271,157 describes use of an identical macrocyclic thioether compound as a ripening agent for silver halide grains. The described compounds may comprise two sulfur and two to four oxygen atoms. However, as is shown below by comparative data, compounds falling within the disclosure of these patents do not provide levels of silver halide crystalline growth modification which are obtained with compounds of this invention.

European Patent Application No. 216,973, published Apr. 8, 1987, describes silver halide growth modifying agents which are macrocyclic polyether compounds comprising at least 1 oxygen atom and at least 3 sulfur atoms. However, as is shown below, such polyether compounds are so strongly adsorbed at silver halide surfaces they decrease, and actually reverse, the characteristic negative surface charge on the silver halide grains.

Although these prior art references describe compounds which are able to modify silver halide crystal growth, the effectiveness of such compounds is not fully satisfactory from a commercial viewpoint. Accordingly, there is an on-going search for compounds which are able, more effectively, to modify the growth of silver halide crystals.

This invention is directed to a photographic element comprising a radiation sensitive silver halide emulsion layer and a macrocyclic ether compound, wherein the ring structure, which comprises more than 12 but less than 30 total ring atoms, comprises (a) more than 2 and less than 10 oxygen atoms and at least one of (b) from 1 to 4 selenium atoms and (c) 1 or 2 sulfur atoms, with the proviso that when the macrocyclic ring contains no selenium atoms the sulfur atoms present in the ring are separated, one from another, by a divalent alkylene chain comprising less than 6 carbon atoms.

The photographic element described herein contains a macrocyclic ether compound which yields a stable, pH-independent, water soluble silver complex. The macrocyclic ether compound exhibits superior silver halide growth-modifying properties.

A preferred macrocyclic ether compound useful in this invention comprises from about 15 to about 21 total ring atoms.

While the number of oxygen atoms contained in the macrocyclic ring is more than 2 but less than 10, a preferred number of ring oxygen atoms is from about 3 to about 7. These oxygen atoms are present as divalent alkylene oxide units where such units preferably comprise from 1 to 3 ring carbon atoms.

Preferred macrocycle compounds suitable for use in this invention can be represented by the structural formula:

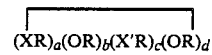

wherein:
- X and X' are each, independently, sulfur or selenium atoms;
- R is a divalent alkylene group having less than 6 carbon atoms, which is optionally substituted;
- a and c are 1, 2 or 3; and
- b and d are 0, 1, 2 or 3.

When X and X' are both sulfur, b is 0 and a and c are each 1.

The divalent alkylene groups represented by R preferably comprise 1 to 3 carbon atoms and most preferably are ethylene groups. The alkylene groups can be substituted with alkyl or alkoxy groups having from 1 to 4 carbon atoms, with halogen atoms or with amino or substituted amino groups.

Particular illustrations of macrocyclic polyether compounds of this invention include the following:

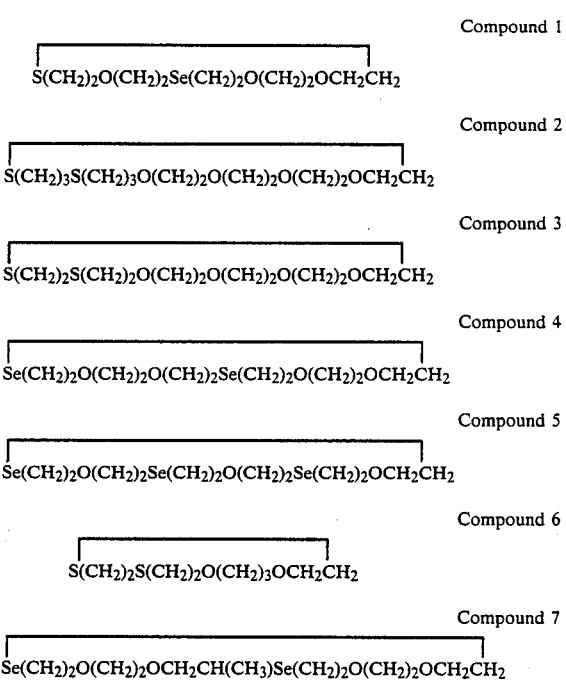

It is believed the effectiveness of the described macrocyclic ether compounds is due to an increased solvation action on silver halides, and results from formation of complexes with Ag+ ions. These complexes have the characteristics of being thermodynamically stable and kinetically labile, i.e., they are rapidly disassociated and recomplexed. This property is believed to enhance chemical ripening activity.

The synthesis of macrocyclic ether compounds with thia substituents is well known and has been described in J. Bradshaw and J. Hui (J. Heterocyclic Chem., 11, 649, 1974). Analogous macrocyclic ether compounds with selena substituents have not previously been reported. However, their preparation follows the general procedures already established for the thia compounds. This is illustrated below by the synthesis of 1,10-diselena-4,7,13,16-tetraoxacyclooctadecane (Compound 4).

SYNTHESIS OF COMPOUND 4

1,8-dichloro-3,6-dioxaoctane (37.4 g) and NaBH$_4$ (14.8 g) were combined in 0.6 l ethanol to which selenium (15.8 g) was added incrementally. The exothermic reaction remained colorless until about half of the selenium was added. When the reaction turned yellow, the solution was first refluxed for about 3 hours and then the balance of the selenium was added while refluxing was continued. Additional 0.5 g increments of NaBH$_4$ were introduced until the brown reaction mixture turned pale. After 15 more hours refluxing, followed by decanting from a gummy precipitate, water was added. All water-insoluble solids were combined and the liquids evaporated to dryness. These residues were extracted with several portions of hot ethanol. After cooling, filtering and evaporating the solvent, a pale yellow oil (12.6 g) resulted and was allowed to crystallize after addition of 10 ml ethyl acetate. Upon recrystallization, 2.8 g colorless crystals, m.p. 92°–93°, were collected, Analysis showed 36.8% carbon, 6.2% hydrogen, 40.5% selenium which agreed with the values calculated for Compound 4.

The compounds described herein can be used as silver halide solvents and to modify the growth of silver halide grains in the approximate range pAg 6 to 11 and pH 2 to 8. The useful concentration range for silver halide ripening is from about $10^{-6}$ to about $10^{-1}$ mole/silver mole, with concentrations of from about $10^{-4}$ to about $10^{-2}$ being preferred. The ripening agents described herein can be used singly or in combination with other ripening agents or with growth modifying, spectral sensitizing, stabilizing or antifogging agents.

The silver halide grains can be of any halide composition (e.g., silver bromide, silver bromoiodide, silver chloride, silver chlorobromoiodide), of any size (e.g., coarse or fine) and can be of any regular or irregular shape (e.g., spherical, regular cubic, regular octahedral, cubo-octahedral, or tabular octahedral) known to be useful in photography.

Conventional vehicles can be used, such as those described in *Research Disclosure (RD), Vol.* 176, December 1978, Item 17643, paragraph IX. Silver halides can be spectrally sensitized as described in paragraph IV of the same RD reference.

The improvements of this invention can be applied to black and white photography (including radiography) or, preferably, to color photography, to form silver images and/or dye images by selective dye destruction, formation or physical elimination, as described in paragraph VII of the above-mentioned RD reference. Preferred color photographic elements are those that form dye images by means of color developing agents and dye forming couplers. Use of these elements involves exposure and processing in any known manner as described in paragraphs XVIII and XIX of the above-mentioned RD reference.

The following examples are presented as further illustrations of the invention.

EXAMPLE 1

Ripening was carried out in a 8 mM AgBr emulsion of rounded cubes with 0.05 mM test compound for 17 hours at 25° C. near pH3 and pBr3. The emulsion also contained 0.1% ossein gelatin (isoelectric point 4.9), 28 mM KNO$_3$ and 30% methanol. The resulting AgBr crystal population was sized from electronmicrographs. Resulting data were expressed in average equivalent circular diameters (ECD) of the number-weighted particles.

TABLE I

| Experiment | Additive | ECD, μm | Relative Size |
|---|---|---|---|
| 1. Control | None | 0.186 | 1.0 |
| 2. Prior Art | Thioether A* | 0.209 | 1.22 |
| 3. Invention | Compound 4 | 0.348 | 1.85 |

*1,10-dithia-4,7,13,16-tetraoxacyclooctadecane of U.S. Pat. Nos. 3,062,646 and 3,271,157.

Table I shows that, unlike the low ripening activity from the prior art macrocyclic thioether compound, the corresponding selena analog (Compound 4) nearly doubled the AgBr crystal diameter.

EXAMPLE 2

Turbidimetry was used to evaluate the effect, by additives, on Ostwald ripening rates of small-particle silver halide dispersions. Details of this method are given by Oppenheimer, James and Hertz in "*Particle Growth in Suspensions*", A. L. Smith, Ed., Academic Press, New York, 1973, p. 159 and by Donohue and Herz, *Photogr. Sci. Eng.*, 25, 92 (1981).

Rate measurements were carried out at 22° C. with 8 mM AgCl (ca. 50 nm) dispersed in 0.12% ossein gelatin (isoelectric point 4.9) with contained 8 mM KNO$_3$, 1 mM KCl and 0.05 mM test compound at pH 5.8. Turbidity at 436 nm was determined as a function of time and the linear plot thus obtained, yielded the rate measurement of AgCl ripening (or growth rate) as listed in accompanying Table 2.

TABLE 2

| Experiment | Additive | Relative AgCl Growth Rate |
|---|---|---|
| 1. Control | None | 1 |
| 2. Prior Art | Thioether B* | 97 |
| 3. Invention | Compound 3 | 330 |

*1,7-dithia-4,10,13,16-tetraoxacyclooctadecane which falls within the disclosures of U.S. Pat. Nos. 3,062,646 and 3,271,157.

From the above data it is apparent that a macrocyclic ether compound of this invention is a much more rapidly acting promoter of AgCl growth than is its prior art analog.

EXAMPLE 3

Ripening was carried out in a 8 mM AgCl emulsion consisting of cubes (ca. 0.52 μm edgelength) with 0.4 mM test compound for 17.5 hours at 25°, pH 6. The emulsion also contained 0.03% ossein gelatin (isoelectric point 4.9), 8 mM KNO$_3$ and 10 mM KCl. The resulting AgCl crystal population was sized from electronmicrographs. Resulting data were expressed in average equivalent circular diameters (ECD) of the number-weighted particles and are recorded in Table 3.

TABLE 3

| Experiment | Additive | ECD, μm | Relative Size |
|---|---|---|---|
| 1. Control | None | 0.59 | 1 |

TABLE 3-continued

| Experiment | Additive | ECD, μm | Relative Size |
| --- | --- | --- | --- |
| 2. Prior Art | Thioether A* | 0.57 | 0.96 |
| 3. Invention | Compound 3 | 0.95 | 1.6 |

*Structure given in Example I

From these results it is clear that under the described conditions a macrocyclic compound of this invention increased AgCl particle size by 60%, yet such growth was not obtained with the isomeric compound of the prior art.

EXAMPLE 4

Electrophoresis was employed to evaluate adsorption of molecules by monitoring their influence on AgBr/Br- surface charge with the previously described procedure (W. Gardener, D. Wrathall and A. Herz, *Photogr. Sci. Eng.*, 21, 325, 1977). Electrophoretic mobilities were measured with about 1 mM AgBr at pH3, pBr3, 25 C., which contained 0.05 mM of a macrocyclic polyether compound as described below in Table 4.

TABLE 4

| Experiment | Additive | Mobility, Micron Sec$^{-1}$/ Volt CM$^{-1}$ |
| --- | --- | --- |
| 1. Control | None | $-4.6 \pm 1.2$ |
| 2. Prior Art | Thioether C* | $+4.2 \pm 0.9$ |
| 3. Prior Art | Thioether D* | $+3.0 \pm 0.7$ |
| 4. Invention | Compound 4 | $-2.9 \pm 0.4$ |

*Thioether Compounds C and D are described in Published European Patent Application No. 216,973. Compound C is 1,4-dioxa-7,10,13-trithiacyclopentadecane and compound D is 1,4,7-trioxa-10,13,16-tri-thia-cyclooctadecane.

The data in Table 4 demonstrate that in contrast to Compound 4 of this invention, macrocyclic polyether Compounds C and D, with more than two sulfur atoms molecule, not only diminished the negative charge of AgBr/Br-, but actually reverse that substrate's polarity and cause it to be cationic. These results show a large and unexpected difference in adsorption properties of variously substituted macrocyclic polyether compounds.

This invention has been described in detail with particular reference to preferred embodiments thereof, but it will be understood that variations and modifications can be effected within the spirit and scope of the invention.

What is claimed is:

1. A photographic element comprising a radiation sensitive silver halide emulsion layer and a macrocyclic ether compound wherein the ring structure comprises more than 12 but less than 30 total ring atoms, which ring atoms comprise (a) more than 2 and less than 10 oxygen atoms and at least one of (b) from 1 to 4 selenium atoms and (c) 1 or 2 sulfur atoms, with the proviso that when the macrocyclic ring contains no selenium atoms the sulfur atoms present in the ring are separated one from another by a divalent alkylene chain comprising less than 6 carbon atoms.

2. The photographic element of claim 1 wherein said macrocyclic ring structure comprises from 15 to about 21 atoms.

3. The photographic element of claim 1 wherein there are from 3 to about 7 ring oxygen atoms.

4. The photographic element of claim 3 wherein said oxygen atoms are present as divalent alkylene oxide units.

5. The photographic element of claim 4 wherein said alkylene oxide units comprise from 1 to 3 carbon atoms.

6. The photographic element of claim 1 wherein said macrocyclic compound has the structural formula:

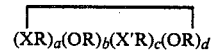

wherein:
X and X' are each, independently, sulfur or selenium atoms;
R is a divalent alkylene group having less than 6 carbon atoms;
a and c are 1, 2 or 3; and
b and d are 0, 1, 2 or 3.

7. The photographic element of claim 1 wherein said compound is present in said emulsion layer in an amount of from about $10^{-6}$ to about $1 \times 10^{-1}$ mole/silver mole.

8. The photographic element of claim 7 wherein said ether compound is present in said emulsion layer in an amount of from about $1 \times 10^{-4}$ to about $10^{-2}$ mole/silver mole.

9. The photographic element of claim 1 wherein said macrocyclic ether compound has the structural formula:

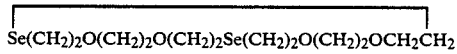

10. The photographic element of claim 1 wherein said macrocyclic ether compound has the structural formula:

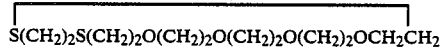

* * * * *